US00PP09161P

United States Patent [19]

Harkness

[11] Patent Number: Plant 9,161

[45] Date of Patent: Jun. 13, 1995

[54] FLORIBUNDA ROSE PLANT NAMED HARWELCOME

[75] Inventor: J. L. Harkness, Southwold, England

[73] Assignee: Weeks Wholesale Rose Grower, Inc., Upland, Calif.

[21] Appl. No.: 176,131

[22] Filed: Dec. 22, 1993

[51] Int. Cl.[6] ..... A01H 5/00

[52] U.S. Cl. ..... Plt./22

[58] Field of Search ..... Plt. 22, 11, 16, 17, Plt. 25

*Primary Examiner*—Howard J. Locker

*Attorney, Agent, or Firm*—Christie, Parker & Hale

[57] ABSTRACT

A new variety of Floribunda rose suitable for garden decoration, having flowers of blended orange coloration.

1 Drawing Sheet

BACKGROUND OF THE INVENTION

This invention relates to a new and distinct variety of Floribunda Rose. The varietal denomination of the new variety is 'Harwelcome.' The plant is a bushy upright seedling cultivated for outdoor garden decoration and is moderately hardy. It was bred in Hitchin, Hertsfordshire, United Kingdom, and has as its seed parent the variety known as 'Southampton' and as its pollen parent the variety known as 'Remember Me.'

SUMMARY OF THE INVENTION

Among the features which distinguish the new variety cv. Harwelcome from other presently available and known commercial rose cultivars are the following combination of characteristics: brightly colored flowers of blended apricot and orange, abundance of highly glossed bright green foliage often edged with reddish pigment and unusually high degree of resistance to blackspot. Cv. 'Harwelcome' may be propagaged by cuttings, budding, grafting, layering and tissue culture.

Asexual propagation of the new variety by budding as performed in Kern County and Upland, Calif., shows that the foregoing and other distinguishing characteristics come true to form and are established and transmitted through succeeding propagations.

COMPARISON WITH PARENT VARIETIES

The new rose may be distinguished from its seed parent, 'Southampton' by the following combination of characteristics: whereas the new cultivar bears flowers of a blended apricot and orange coloration, the seed parent bears flowers of an apricot coloration; flowers of the seed parent have significantly more fragrance than the new seedling; and whereas 'Harwelcome' has a bushy upright medium height growth habit with very full branching, 'Southampton' has a significantly taller habit with much less branching.

The new variety may be distinguished from its pollen parent, 'Remember Me' by the following combination of characteristics: whereas the new seedling bears flowers of an apricot and orange blend coloration, the pollen parent bears flowers of a significantly darker orange coloration combined with some near brown tonations; flowers of 'Remember Me' have about 20 petals, whereas 'Harwelcome' flowers have significantly higher petalation (25 to 30); and whereas the pollen parent is classified as a Hybrid Tea, the new cultivar is properly classified as a Floribunda.

BRIEF DESCRIPTION OF THE ILLUSTRATION

The accompanying photograph illustrates the plant in color and shows the flowering thereof from bud to full bloom depicted in color as nearly correct as it is possible to make in a color illustration of the character. Throughout this specification, names are values based upon the Colour Chart of The Royal Horticultural Society of London, England, except where common terms of color definition are employed.

DESCRIPTION OF THE NEW VARIETY

The following descriptive matter pertains to roses of the new cultivar grown outdoors in August 1993 in Upland, Calif. Phenotypic expression may vary with environmental, cultural and climatic conditions, as well as differences in conditions of light and soil.

FLOWER

The new variety bears its flowers sometimes singly, usually three to four or more per stem. Flowers are borne in regular flat to rounded clusters on strong medium to long stems for the class. Outdoors the plant blooms very abundantly and nearly continuously during the growing season. The flowers have a slight fruity fragrance. Stem length is medium to long, generally about 25 to 42 cm.

BUD

The peduncle is of short to average length for the class, of average caliper, and usually erect. It is almost entirely smooth with some stipitate glands and hairs. Peduncle color is between 138A and 144A, sometimes lightly blushed on the side facing the sun with near 178C. The peduncle length is short to average, about 3 to 5 cm. The green bud is moderately small, about 1.5 to 2 cm at the widest point and about 2.5 to 3 cm in length. The opening bud is about 2 to 2.5 cm at the widest point and about 2.5 to 3 cm in length.

Before the calyx breaks, the bud is of moderately small size for the class, medium in length, and pointed to ovoid in shape. The surface of the bud bears some stipitate glands and fine hairs, with slender foliaceous parts extending beyond the tip of the bud equal to ¼ or more of its length. Bud color is between 138A and 144A, sometimes lightly blushed on the side facing the sun with near 178C, before sepals divide.

The inner surface of the sepals is covered with fine wooly tomentum; sepal margins are lined with many stipitate glands and hairs.

As the first petal opens, the bud is somewhat small to medium size for the class, medium in length, and somewhat pointed to ovoid in form. The color of the outside of the newly opened petals is between 40B and 47C with a moderately sized basal attachment zone of between 7A and 12A. The color of the inside surfaces of the newly opened petals is between 41A and 31A with a basal attachment zone of similar size and coloration. Basal attachment zone as used herein refers to the zone at the point of petal attachment. The bud does open up well and is not prevented from opening by cold, hot, wet or dry weather.

BLOOM

When fully open, the bloom is medium sized for the class, ranging from 9 to 10.5 cm. in diameter. Petalage is double with 25 to 30 petals and 1 to 5 petaloids arranged regularly. When partially open, the bloom form is somewhat cupped and the petals are somewhat undulated. When fully open, the bloom form is somewhat more flat to cupped and the petals are moderately loosely undulated to reflexed backward.

PETALS

The petals are of moderately heavy substance and of medium thickness, with inside surfaces slightly velvety and outside slightly satiny. The outer petals are very broadly obovate in shape with a mostly rounded apex. The intermediate petals are somewhat obovate to nearly round in shape with the apex usually rounded to flat. The inner petals are more narrowly obovate in shape.

NEWLY OPENED FLOWER

The outside surface of the outer petals is between 40C and 39C with a moderately large basal attachment zone of near 12A. The majority of the inside surface of the outer petals is between 33B and 26C with a basal attachment zone of similar size and coloration. Toward the outer edges of the petals, the coloration blushes darker to between 42B and 39A.

The outside surface of the intermediate and inner petals is between 28D and 33B with a moderately large basal attachment zone of near 12B. The inside surface of the intermediate and inner petals is between 33C and 26C. There is no blushing to a darker color.

The general tonality of the newly opened flower is between 33C and 26C with darker tones around the outer petals of between 42B and 39A.

THREE DAY OLD FLOWER

The outside surface of the outer and inner petals is between 33C and 41C with a moderately large basal attachment zone of near 11A. The inside surface of the outer and inner petals is between 42C and 39B with a basal attachment zone of similar size and coloration.

The general tonality of the three day old flower is between 42C and 39B.

On the spent bloom, the petals usually drop off cleanly and are not particularly affected by cold, hot, wet or dry weather.

In August, blooms on the bush growing in the garden generally last from three to four or more days. Cut roses grown outdoors and kept at normal indoor living temperatures generally last from four to five or more days.

MALE REPRODUCTIVE ORGANS

Stamens are average to many in number and are arranged regularly about the pistil. The filaments are of irregular medium to long length, most with anthers. The anthers are moderately small for the class and all open approximately at the same times. Anther color is near 26A when immature and near 172A at maturity. Pollen is moderate to abundant and near 15C in color.

FEMALE REPRODUCTIVE ORGANS

Pistils are moderately abundant in number (approximately 90). The styles are somewhat uneven, moderately short in length, average in caliper, and moderately bunched. Stigma color is near 10D. Style color is near 42C. Ovaries are usually all enclosed in the calyx.

Hips are somewhat short in length, very globular in form, and become near 30C in color when mature. The hip surface is very smooth with somewhat thick fleshy walls. The sepals fall away soon after seed set. Seeds are moderately few in number (approximately 8 to 13), and average in size.

FOLIAGE

The compound leaves are usually comprised of three to five and sometimes seven leaflets and are borne abundantly. The leaves are of moderate size for the class, very heavy to leathery in texture, and very glossy in finish. The leaflets are shaped moderately ovate to ovoid with somewhat acute apices and somewhat round bases. Their margins are usually doubly serrate. Leaflets are about 3.5 to about 7 cm in length and about 2 to about 4.5 in width at the widest point. Leaves are about 9 to 13 cm in length and about 7 to about 9 cm in width at the widest point.

The upper surface of the very mature leaf is between 137A and 139A. The under surface of the very mature leaf is between 191B and 194A. The upper surface of a newly mature leaf is between 137B and 137C and often very finely edged with between 183A and 175A. The upper surface of the young leaf is between 146C and 137D, sometimes lightly suffused and often edged with between 183A and 175A. The under surface of the young leaf is between 146C and 137D, usually heavily suffused with between 183C and 175C.

The rachis is average in caliper and moderately rough to grooved with some hairs and stipitate glands on the edges of the upper side. The underside of the rachis is moderately rough with some stipitate glands and few prickles.

The stipules are of medium width, short to medium length, and have straight points that usually turn out at an angle of less than 90 degrees.

The plant displays a very high degree of resistance to blackspot and an above average degree of resistance to powdery mildew and rust as compared to other commercial varieties grown under comparable conditions in Upland, Calif.

GROWTH

The plant has a bushy upright medium height habit with very full branching. It displays very vigorous growth and the canes are of medium to heavy caliper for the class. The plant achieves a medium height of about 105 to 130 cm and a width of about 90 to 115 cm.

The color of the major stems are near 146B. They bear several large prickles which are moderately long for the class. The large prickles are almost straight with a somewhat short narrow base; prickle color is near 177A. The major stem bears many small prickles of similar shape and coloration.

The color of the branches are between 144A and 138B. They bear several large prickles which are moderately long for the class. The large prickles are almost straight with a somewhat short narrow base; prickles color is near 164B. The branches bear several small prickles of similar shape and coloration and some coarse hairs.

The color of the new shoots is between 144A and 138B, sometimes leightly suffused with near 183C. They bear several large prickles which are moderately long for the class. The large prickles are almost straight with a somewhat short narrow base; prickle color is between 183C and 175B. The shoots also bear many small prickles of similar shape and coloration and many coarse hairs.

I claim:

1. A new and distinct variety of Floribunda rose plant substantially as described and illustrated herein.

* * * * *

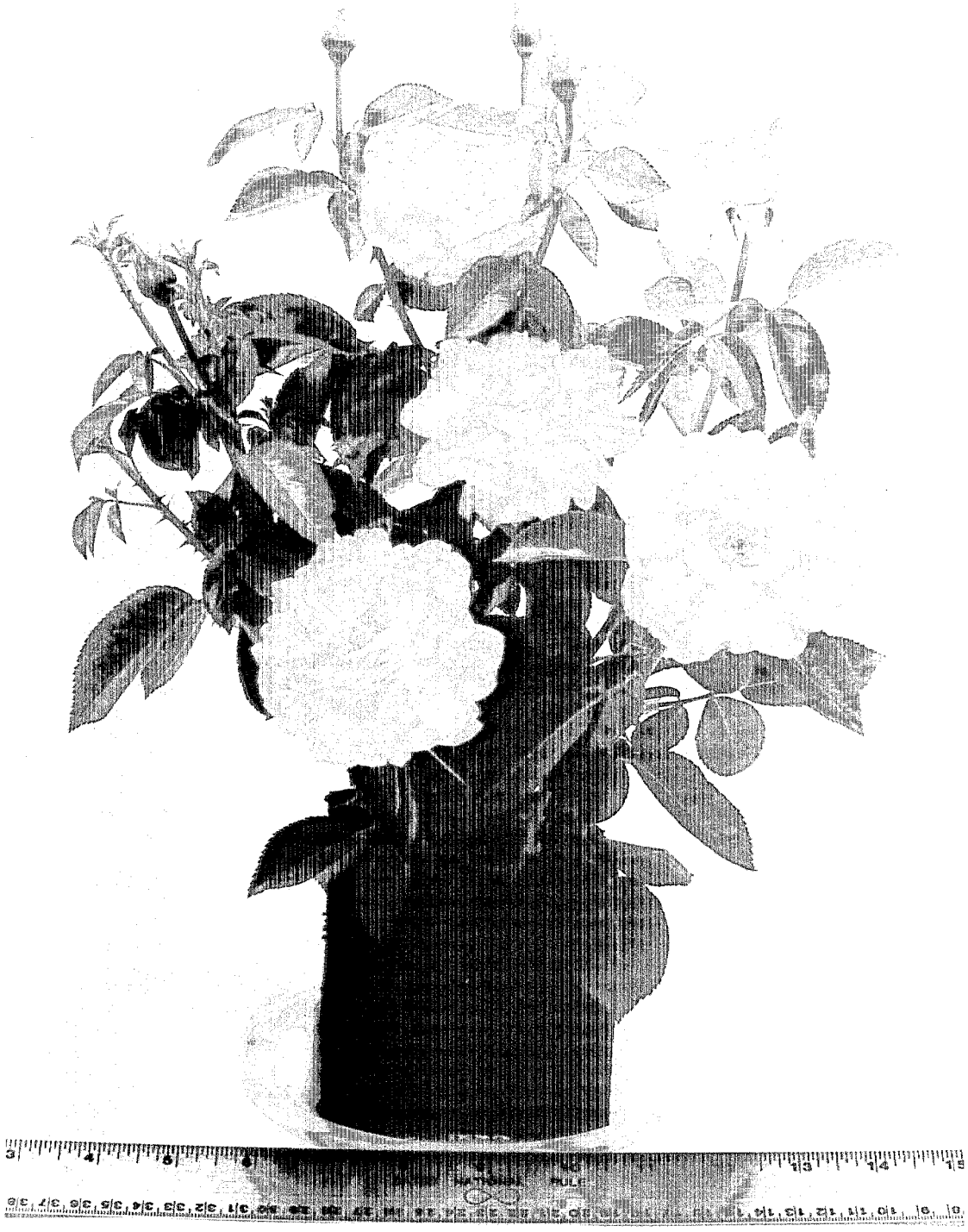

UNITED STATES PATENT AND TRADEMARK OFFICE

CERTIFICATE OF CORRECTION

PATENT NO. : Plant 9,161

DATED : June 13, 1995

INVENTOR(S) : J.L. Harkness

It is certified that error appears in the above-indentified patent and that said Letters Patent is hereby corrected as shown below:

Column 3, line 39, change "39C" to -- 39A --.

Column 5, line 12, change "leightly" to -- lightly --.

Signed and Sealed this

Sixteenth Day of January, 1996

*Attest:*

*Attesting Officer*

BRUCE LEHMAN

*Commissioner of Patents and Trademarks*